United States Patent
Rowell et al.

(10) Patent No.: US 9,709,583 B2
(45) Date of Patent: Jul. 18, 2017

(54) MALDI/SELDI ANALYSIS OF COMPLEX MIXTURES COMPRISING HYDROPHILIC AND HYDROPHOBIC ANALYTES

(75) Inventors: Frederick Rowell, Durham (GB); Jan Ma, Singapore (SG); Angelina Yi Mei Lim, Singapore (SG)

(73) Assignees: Frederick Rowell, Durham (GB); NANYANG TECHNOLOGICAL UNIVERSITY, Singapore (SG)

( * ) Notice: Subject to any disclaimer, the term of this patent is extended or adjusted under 35 U.S.C. 154(b) by 271 days.

(21) Appl. No.: 13/060,249

(22) PCT Filed: Aug. 20, 2009

(86) PCT No.: PCT/GB2009/051037
§ 371 (c)(1),
(2), (4) Date: Feb. 22, 2011

(87) PCT Pub. No.: WO2010/020812
PCT Pub. Date: Feb. 25, 2010

(65) Prior Publication Data
US 2011/0151569 A1   Jun. 23, 2011

(30) Foreign Application Priority Data
Aug. 20, 2008   (GB) .................................. 0815212.6

(51) Int. Cl.
*G01N 24/00*   (2006.01)
*G01N 35/00*   (2006.01)
(Continued)

(52) U.S. Cl.
CPC ............ *G01N 35/0098* (2013.01); *G01N 1/40* (2013.01); *G01N 33/585* (2013.01);
(Continued)

(58) Field of Classification Search
CPC ........ C12Q 2545/114; C12Q 2537/143; C12Q 1/6837; C12Q 2563/167; C12Q 2563/155;
(Continued)

(56) References Cited

U.S. PATENT DOCUMENTS

| 7,183,544 B2 | 2/2007 | Boschetti et al. ............ 250/288 |
| 2004/0018611 A1 | 1/2004 | Ward et al. ................ 435/287.2 |

(Continued)

FOREIGN PATENT DOCUMENTS

| WO | 00/50172 | 8/2000 |
| WO | 01/84143 | 11/2001 |

(Continued)

OTHER PUBLICATIONS

Safarik and Safarikova "Magnetic techniques for the isolation and purification of proteins and peptides", BioMagnetic Research and Technology, 2004, v. 2, No. 7, pp. 1-17.*

(Continued)

*Primary Examiner* — Yelena G Gakh
(74) *Attorney, Agent, or Firm* — Seed IP Law Group LLP

(57) ABSTRACT

The present disclosure relates to the identification of components in a sample based on the chemical nature of the component. In particular, although not exclusively, the present disclosure relates to the identification of hydrophobic and hydrophilic components using a mass spectrometric technique. The present invention also relates to kits and products used in the identification of the components, as well as other subject matter.

9 Claims, 7 Drawing Sheets

(51) Int. Cl.
G01N 1/40 (2006.01)
G01N 33/58 (2006.01)
G01N 33/68 (2006.01)
H01J 49/04 (2006.01)
G01N 1/04 (2006.01)
G01N 1/10 (2006.01)
G01N 1/18 (2006.01)
G01N 1/28 (2006.01)

(52) U.S. Cl.
CPC ...... *G01N 33/6848* (2013.01); *H01J 49/0418* (2013.01); *G01N 1/04* (2013.01); *G01N 1/10* (2013.01); *G01N 1/18* (2013.01); *G01N 1/28* (2013.01); *G01N 2458/15* (2013.01); *Y10T 436/143333* (2015.01); *Y10T 436/24* (2015.01); *Y10T 436/25375* (2015.01)

(58) Field of Classification Search
CPC ........ C12Q 2563/137; C12Q 2563/143; C12Q 2565/627; G01N 33/6848; G01N 35/00; G01N 35/0098; G01N 2021/6441; G01N 35/1065
See application file for complete search history.

(56) References Cited

U.S. PATENT DOCUMENTS

| | | | |
|---|---|---|---|
| 2004/0219066 A1 | 11/2004 | Kraus, Jr. et al. | 422/72 |
| 2004/0229346 A1 | 11/2004 | Kohara et al. | 435/287.2 |
| 2005/0155861 A1 | 7/2005 | Guzman | |
| 2005/0191677 A1* | 9/2005 | Franzen et al. | 435/6 |
| 2006/0084089 A1* | 4/2006 | Fort et al. | 435/6 |
| 2007/0166835 A1* | 7/2007 | Bobrow et al. | 436/174 |
| 2007/0196656 A1* | 8/2007 | Rowell | 428/403 |

FOREIGN PATENT DOCUMENTS

| | | |
|---|---|---|
| WO | 2005/010527 | 2/2005 |
| WO | 2007/017700 | 2/2007 |
| WO | 2007/017701 | 2/2007 |
| WO | 2008/035124 | 3/2008 |

OTHER PUBLICATIONS

Chen and Chen, "Affinity-based mass spectrometry using magnetic iron oxide particles as the matrix and concentrating probes for SALDI MS analysis of peptides and proteins", Anal. Bioanal. Chem., 2006, v. 386, pp. 699-704.*

Lin et al., "Affinity Capture Using Vancomycin-Bound Magnetic Nanoparticles for the MALDI-MS Analysis of Bacteria", Anal. Chem., 2005, v. 77, pp. 1753-1760.*

Tan et al. "Specific capture of phosphopeptides on matrix-assisted laser desorption/ionization time-of-flight mass spectrometry targets modified by magnetic affinity nanoparticles", Rapid Comm. Mass Spectrom., 2007, v. 21, pp. 2407-2414.*

Arkles "Hydrophobicity, Hydrophilicity and Silanes", Reprinted with permission from the Oct. 2006 issue of Paint & Coatings Industry magazine, pp. 1-10.*

Crecelius et al., "Thin-layer chromatography-matrix-assisted laser desorption ionization-time-of-flight mass spectrometry using particle suspension matrices," *Journal of Chromatography A*, 958:249-260, 2002.

Menzel et al., "Photoluminescent CdS/Dendrimer Nanocomposites for Fingerprint Detection," *J. Forensic Sci.* 45(4):770-773, 2000.

Menzel et al., "Photoluminescent Semiconductor Nanocrystals for Fingerprint Detection," *J. Forensic Sci.* 45(3):545-551, 2000.

Tapec et al., "Development of Organic Dye-Doped Silica Nanoparticles for Bioanalysis and Biosensors," *J. Nanosci. Nanotech.* 2(3/4):405-409, 2002.

Safarik, I. et al., "Magnetic techniques for the isolation and purification of proteins and peptides," Biomagn Res Technol. 2(7), 17 pgs., Nov. 26, 2004.

* cited by examiner

MALDI/SELDI ANALYSIS OF COMPLEX MIXTURES COMPRISING HYDROPHILIC AND HYDROPHOBIC ANALYTES

The present disclosure relates to the identification of components in a sample based on the chemical nature of the component. In particular, although not exclusively, the present disclosure relates to the identification of hydrophobic and hydrophilic components using a mass spectrometric technique. The present invention also relates to kits and products used in the identification of the components, as well as other subject matter.

BACKGROUND

Biological samples generally consist of complex mixtures of components that include both hydrophobic and hydrophilic compounds of interest. One method that has been adopted to separate and pre-concentrate these types of components is based on the use of spots of affinity materials with differing affinities for hydrophobic, hydrophilic, charged and uncharged compounds, on the surface of a planar platform, typically a plate. This plate is designed to be compatible with a mass spectrometric system that can interrogate the constituents which become concentrated on the surface of such spots. The surface spots attract constituents due to hydrophobic, hydrophilic, charge transfer, ionic, metal-chelate affinity and dye-affinity interactions and each spot has a different composition designed to use one example of such interactions (see e.g. U.S. Pat. No. 7,183,544)

In practice, a solution of the mixture of analytes within a biological matrix which is, for example, serum, plasma, saliva, or urine, is applied to the surface of the plate where selective binding takes place at one or more spots during an incubation step. The plate is then washed to remove unbound constituents and following drying, the plate is interrogated via the mass spectrometer to produce ions which are then identified via their time of flight/charge to mass ratio within the mass spectrometer. The pattern of distribution that is seen for particular chemicals/biochemicals can be used for diagnostic purposes to identify particular diseases, or for other applications.

A method of analysing constituents of fingerprints using MALDI-TOF-MS is disclosed in WO2007/017701. The particles used in the methods are hydrophobic silica particles which are capable of hydrophobic-hydrophobic interactions with a class of constituents. However, the particles disclosed in WO 2007/017701 tend not to be suited for use in analysing constituents which are not capable of hydrophobic-hydrophobic interactions, for example, peptides or amino acids.

In some embodiments, the method of the present invention enables analysis of a wider range of constituents than the prior art using a mass spectrometric technique.

BRIEF SUMMARY OF THE DISCLOSURE

The present invention relates, at least in part, to a method which utilises a step of pre-adsorption and concentration of components within biological matrices and their subsequent separation on a planar surface. The present invention further includes analysing one or more of the components e.g. with a mass spectrometric technique.

In a first aspect of the present invention, there is provided a method of preparing a sample comprising at least a first target constituent for analysis by a mass spectrometric technique, the method comprising mixing the sample with a first particulate affinity material, wherein said first particulate affinity material is magnetic, to form a magnetic first affinity material/constituent complex; and separating the first affinity material/constituent complex from remainder of the sample by selectively locating at least one magnetic element with respect to the sample. In one embodiment, the constituent is adsorbed onto a surface of the first particulate affinity material.

The method may further comprise carrying out a mass spectrometric technique on the separated first affinity material-constituent complex. In one embodiment, the sample is located on a surface and the first affinity material/constituent complex is moved to a location spaced apart from the remainder of the sample on the surface. The surface may be a plate suitable for use in a mass spectrometric technique. The surface may further contain at least one well, wherein the separated first affinity material/constituent complex is moved to a well. A mass spectrometric technique may then be performed on the separated first affinity material/constituent complex.

In one embodiment, the sample contains at least two target constituents and the method is for preparing the sample in order to enable a mass spectrometric technique to be performed on the at least two target constituents. In one embodiment, the mass spectrometric technique is carried sequentially, that is to say e.g. that a first mass spectrometric technique is carried out on one target constituent, followed by a second mass spectrometric technique is carried out on a further target constituent. In one embodiment, a mass spectrometric technique is performed on at least a portion of the remainder of the sample. The method may further comprise adding a matrix assisting agent to the portion of the remainder of the sample prior to carrying out the mass spectrometric technique.

In one embodiment, the method includes contacting (1) the sample and/or (2) the remainder of the sample left (e.g. which remains) after the first affinity material-constituent complex has been separated from the sample, with a second particulate affinity material to form a second particulate affinity material/constituent complex. In one embodiment, a mass spectrometric technique is performed on the second particulate affinity material/constituent complex.

In one embodiment, a plurality of mass spectrometric techniques may be carried out e.g. when a plurality of target constituents is comprised within the sample. In one embodiment, the method comprises identifying 2, 3, 4, 5, 6 or more target constituents.

In one embodiment, the first particulate affinity material and the second particulate affinity material differ from one another. In one embodiment, the first particulate affinity material and the second particulate affinity material each are capable of forming complexes with different target constituents. The first particulate affinity material and the second particulate affinity material may each independently form a complex with a different target constituent. In one embodiment, the first particulate affinity material differs from the second particulate affinity material in one or more of the following properties; a hydrophobic property, a hydrophilic property, an electrostatic property, a chemical property and polarity. The property in which the affinity materials differ may be a property which is involved in the interaction between the affinity material and the target constituent to form an affinity material/constituent complex.

In one embodiment, the first particulate affinity material includes hydrophobic particles which form complexes with target first constituents, wherein the target first constituents are capable of hydrophobic-hydrophobic interaction. In one embodiment, the first affinity material includes hydrophobic silica particles, which may be formed from combining silane ether monomers and organically modified silane ether monomers in the presence of a hydrolysing agent. Further details of a class of hydrophobic silica particles which may be used in the invention are provided below. In one embodiment, the second particulate affinity material may include hydrophilic particles which form complexes with target second constituents which are capable of hydrophilic interaction. In one embodiment, the second affinity material includes hydrophilic silica particles which may be formed from aminopropyltriethoxysilane (APTES) monomers. Further details of a class of suitable hydrophilic particles are given below.

Alternatively, the converse may be provided: the first particulate affinity material may include hydrophilic particles which form complexes with target first constituents which are capable of hydrophilic interaction and the second particulate affinity material may include hydrophobic particles which form complexes with target second constituents which are capable of hydrophobic-hydrophobic interaction.

In one embodiment, the particles e.g. hydrophilic and/or hydrophobic particles may include organic moieties on their surface. In one embodiment, the constituent is a substance capable of the same interactions as said organic moiety. These organic moieties may differ on particles included in the first affinity material to those included in the second affinity material.

In one embodiment, the method includes contacting and then mixing the first particulate affinity material and the second particulate affinity material with the sample simultaneously. In this embodiment, the second particulate affinity material is preferably not magnetic or less magnetic than the first particulate affinity material.

In one embodiment, the first particulate affinity material and the second particulate material are mixed together in a suspension prior to application to the sample to the sample. The suspension may be an ethanolic or an aqueous suspension.

Alternatively, the method may comprise contacting the first affinity material and the second affinity material with the sample sequentially. In this instance, the second particulate affinity material may be magnetic or paramagnetic. The first particulate affinity material and/or the second affinity material may be applied to the sample in a suspension e.g. an ethanolic suspension.

In one embodiment, either the first and/or the second particulate affinity material are capable of acting as matrix agents in a mass spectrometric technique. The matrix agent may also be considered an enhancing agent. This provides the advantage that a separate matrix agent is not required to perform the mass spectrometric technique. In one embodiment, both the first and the second particulate affinity material are capable of acting as a matrix agent in a mass spectrometric technique.

In this embodiment, the mass spectrometric technique is preferably a technique which utilises a matrix. Thus, in one embodiment, the first and/or the second particulate affinity material are matrix agents. Matrix agents may be capable of (1) embedding and isolating analytes; (2) be vacuum stable; (3) absorbing the laser wavelength; (4) promote analyte ionisation and/or (5) cause analyte desorption upon laser irradiation. In one embodiment, the first and/or the second particulate affinity material comprises silica particles embedded with carbon black. In one embodiment, the mass spectrometric technique is selected from Matrix-assisted laser desorption/ionisation Time-Of-Flight Mass Spectrometry (MALDI-TOF-MS) and Surface-assisted laser desorption/ionisation Time-Of-Flight Mass Spectrometry (SALDI-TOF-MS). Details of other suitable mass spectrometric techniques which form part of the invention are provided below.

In one embodiment, the method further comprises analysing the outcome i.e. the results of the mass spectrometric technique.

In one embodiment, the sample includes a plurality of target constituents and wherein the method involves contacting the sample located on the surface with a plurality of particulate affinity materials, each of which differs from every other particulate affinity material, such that each particulate affinity material binds to a different target constituent to form a plurality particulate affinity material/constituent complexes. The method may further include performing a mass spectrometric technique on each particulate affinity material/constituent complex. In one embodiment, each particulate affinity material differs from other particulate affinity materials by its level of magnetism. Thus, in one embodiment, the method comprises contacting the particulate affinity materials with 2, 3, 4, 5, 6 or more particulate affinity materials, each of which differ from the others.

It will be understood that, in some embodiments in which contact is sequential, the affinity material which contacts the sample second, may contact a remainder of the sample left following separation of the first affinity reagent/constituent complex. Thus, the method may comprise contacting the remainder of the sample with the second affinity material.

In one embodiment, the method further comprises applying the sample to the surface prior to mixing with the first and/or second particulate affinity material. The sample may be applied to the surface as a liquid and then dried. The sample may be for example. air dried.

In a further aspect of the invention, there is provided a kit which includes a first particulate affinity material and a second particulate affinity material, wherein the first particulate affinity material is magnetic, and wherein the first particulate affinity material differs from the second particulate material in one or more of the following properties; hydrophobic properties, hydrophilic properties, electrostatic properties, chemical properties and polarity, and wherein said property is involved in the interaction between the affinity material and the target constituent to form an affinity material/constituent complex.

In one embodiment, the first and/or second affinity material is/are capable of acting as a matrix or enhancing agent in a mass spectrometric technique. The first affinity material may comprise hydrophobic silica particles and the second affinity material may comprise hydrophilic silica particles. In one embodiment, the first and second affinity materials are combined in an ethanolic suspension. In one embodiment, the kit further comprises a magnetic tool for separating the magnetic first particulate affinity material.

In a further aspect of the present invention, there is provided use of at least two different particulate affinity materials in a mass spectrometric technique, wherein the particulate affinity materials differ in properties selected from: hydrophobic, hydrophilic, electrostatic and polarity, wherein optionally each particulate affinity material binds to a different target analyte or constituent.

Thus, the present invention is based, at least in part, on a method which utilises at least two types of particulate affinity materials, each type of affinity material differing from other types of affinity materials by at least one property.

The property in which the affinity materials differ is at least partially responsible for interaction between the affinity material and its affinity partner e.g. a constituent which may be present in the sample. Thus, each affinity material is capable of interaction with an affinity partner (e.g. constituent) that is different to the affinity partner of other affinity materials used in the mixture. In one embodiment, the difference is a difference in a chemical property.

As used herein, the term "affinity partner" is used to describe a constituent which may be present in a sample and which is capable of binding to a component of a corresponding affinity material. In one embodiment, the method comprises the use of more than two particulate affinity materials, each type differing from the other types by at least one property. Thus, the method may comprise contacting the sample and/or the remainder of the sample with 1, 2, 3, 4, 5, 6, 7, 8, 9, 10 or more particulate affinity materials.

In one embodiment, the property is selected from electrostatic properties, hydrophobic properties, hydrophilic properties and polarity.

It will be apparent that the interaction between the affinity material and its affinity partner may not be a total interaction e.g. in certain embodiments less than 100% of the affinity partner binds to its corresponding affinity material. For example, 50%, 55%, 60%, 65%, 70%, 75%, 80%, 85% or 95% of the affinity partner (e.g. target constituent) may bind to its respective affinity material. It may also be the case in some embodiments that a small amount of an affinity partner may interact with an affinity material which is not considered to be its corresponding affinity material.

In any event, the present method is for separating affinity partners (e.g. target constituents) using their differing properties such that a mass spectrometric technique may be carried out to analyse the differing affinity partners and therefore determine their properties. The present invention may also be used to concentrate amounts of constituents present in a sample so as to provide improved analysis of that constituent by a mass spectrometric technique.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

BRIEF DESCRIPTION OF THE DRAWINGS

Embodiments of the present invention are described in more detail below without limitation and with reference to the following drawings.

DETAILED DESCRIPTION

Figure 1:
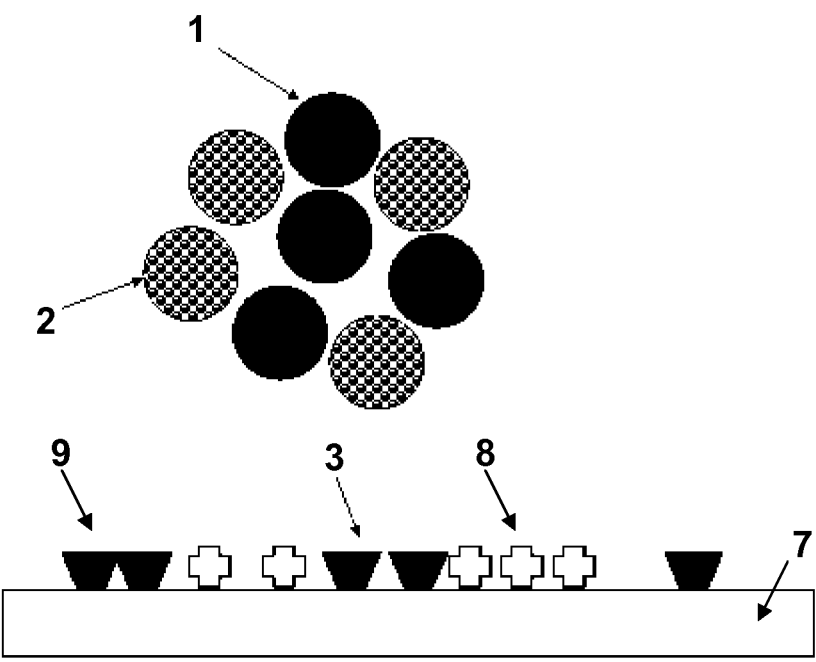
FIG. 1: Schematic representation of an embodiment of the invention in which solid coloured circles (1) represent hydrophilic particles and hatched lines (2) represent magnetisable hydrophobic particles. Crosses represent alanine constituents (8) whilst trapezoids represent squalene constituents (9). A complex mixture of squalene and alanine analytes is shown (3). The complex mixture is situated on a support (7).
Figure 2:
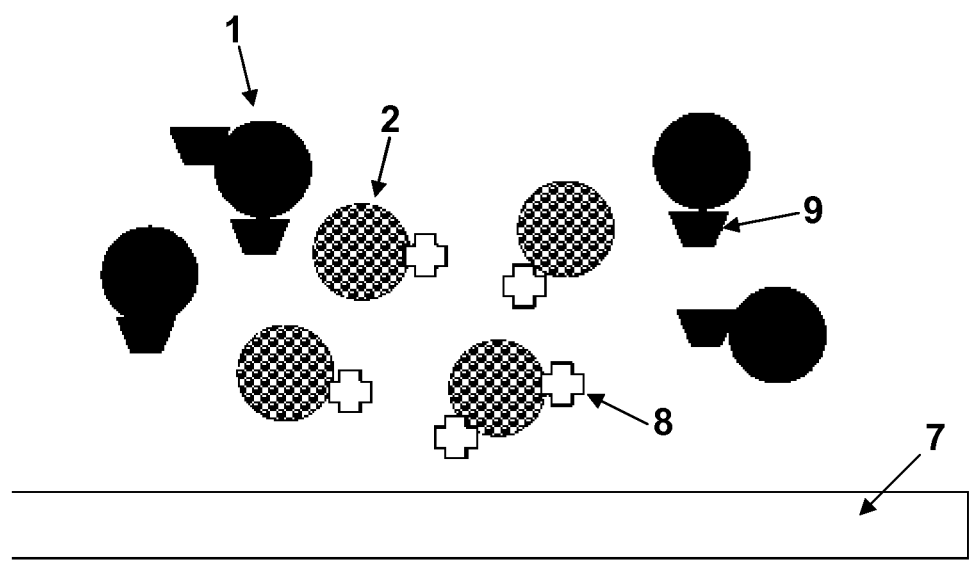
FIG. 2: Schematic representation of an embodiment of the invention showing binding between particle and analyte in solution or suspension. Solid coloured circles (1) represent hydrophilic particles and hatched lines (2) represent magnetisable hydrophobic particles. Crosses represent alanine constituents (8) whilst trapezoids represent squalene constituents (9).
Figure 3:
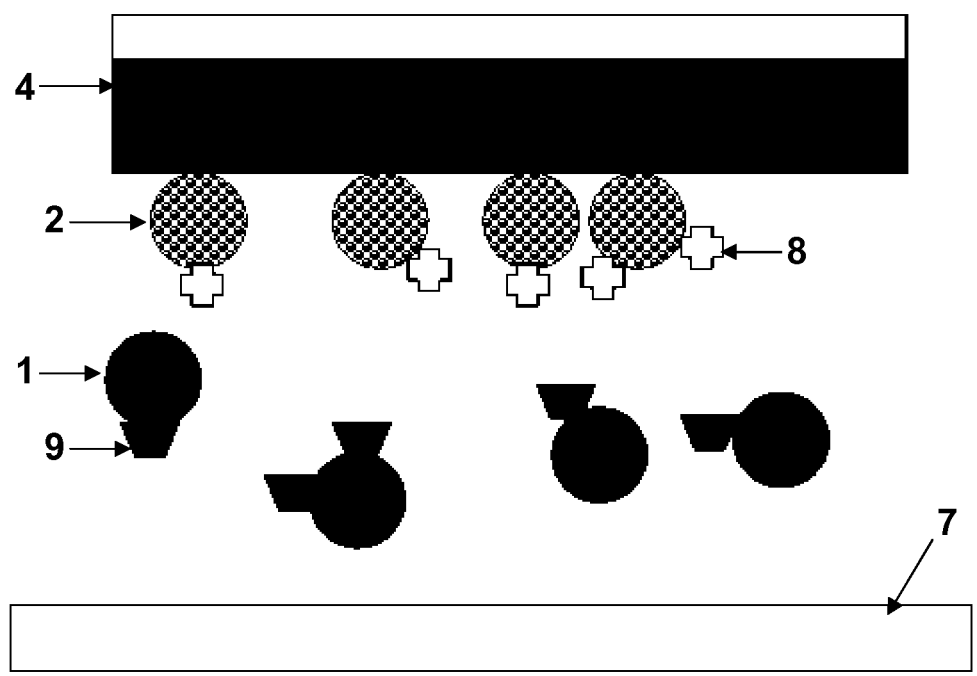
FIG. 3: Schematic representation of an embodiment of the invention showing removal of magnetic particles (2) together with adsorbed analyte on the magnetic particle surface from the sample. Solid coloured circles represent hydrophilic particles (1) and hatched lines represent magnetisable hydrophobic particles (2). Crosses represent alanine constituents whilst trapezoids represent squalene constituents. A magnet is depicted (4).
Figure 4:
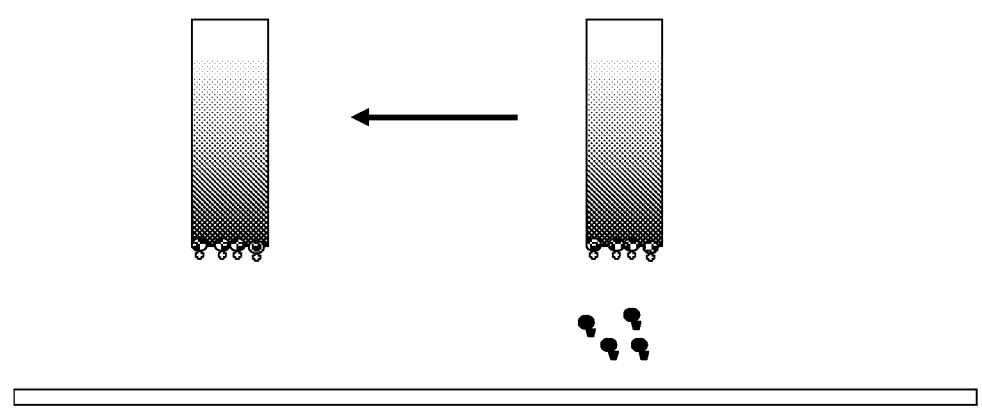
FIG. 4: Schematic representation of an embodiment of the invention including transfer of magnetic particles together with adsorbed analyte on the magnetic particle surface from the sample to a second location on the surface. Solid coloured circles represent hydrophilic particles and hatched lines represent magnetisable hydrophobic particles. Crosses represent alanine constituents whilst trapezoids represent squalene constituents, as before.
Figure 5:
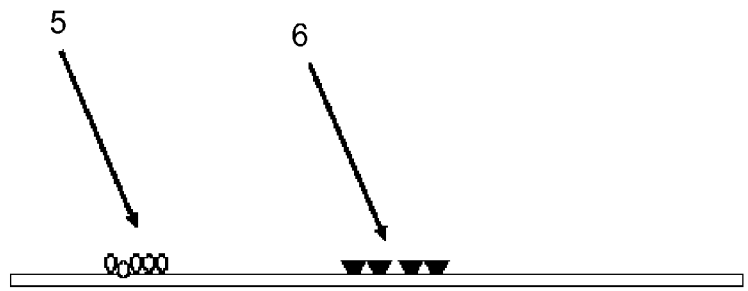
FIG. 5: Schematic representation of an embodiment of the invention showing a mass spectrometric technique being carried out on the separated constituents. A mass spectrometric technique (5) is carried out on the first separated constituents. A mass spectrometric technique (6) is then carried out on the second separated constituents.

Certain aspects of the present invention provide methods and kits for determining properties of constituents of a complex sample e.g. a biological sample. The present invention also provides methods for concentrating one or more constituents present in the sample, which may then provide improved analysis of the constituents.

In a first aspect of the present invention, there is provided a method of preparing a sample for analysis by a mass spectrometric technique, wherein the sample comprises at least a first target constituent, the method comprising mixing the sample with a first particulate affinity material, wherein said first particulate affinity material is magnetic, to form a magnetic first affinity material/constituent complex; and separating the first affinity material/constituent complex from remainder of the sample by selectively locating at least one magnetic element with respect to the sample.

Samples e.g. biological samples, are often complex mixtures of different constituents and the present invention aims to separate at least one of the constituents from the remainder of the sample such that analysis of the constituent may be carried out e.g. by a mass spectrometric technique. The sample may be for example blood, a latent fingerprint residue, an ear print, serum, plasma, saliva, or urine. Alternatively, other samples which may be subject to the methods and/or products of the present invention are environmental fluids e.g. surface water, ground water, sludge, etc. In one embodiment, the sample may be an industrial sample e.g. process fluids such as milk, whey, broth, nutrition solutions, cell culture medium, etc.

The method may further comprise carrying out a mass spectrometric technique on the separated first affinity material-constituent complex. In one embodiment, the sample is located on a surface and the first affinity material/constituent complex is moved to a location spaced apart from the remainder of the sample on the surface. The surface may be a plate suitable for use in a mass spectrometric technique. The surface may further contain at least one well, wherein the separated first affinity material/constituent complex is moved to the well. A mass spectrometric technique may then be performed on the separated first affinity material/constituent complex.

In one embodiment, the method comprises the use of more than one type of particulate affinity material. The types of affinity materials are classifiable into groups according to distinguishable characteristics or differentiation parameters. The groups are substantially discrete (nonoverlapping), with the mean values of the distinguishing characteristics of adjacent groups sufficiently far apart to permit differentiation of each group from the others.

In one embodiment, the method involves adding a mixture of particulate affinity materials, each with different surface determinants, e.g. a suspension of nano-, sub-micro-, or micro-particles, to a sample which has been pre-dispensed as a solution and dried on the surface of a plate or another planar surface. Following addition of the suspension, the sample is reconstituted into the solution or suspension in which the particulate affinity material is applied. In one embodiment, binding between the particles and the constituents (e.g. analytes) occurs which may lead to pre-concentration of specific constituents onto one or more types of particulate affinity material due to the affinity interactions between the particles and the constituents.

In one embodiment, the first and second particulate affinity materials are physically separated on the planar surface of the platform. Following evaporation of solvent used to apply the particles, the separated types of affinity material/constituent complexes are located at various sites on the surface. Thus the method includes interrogating the separated complexes separately in turn via mass spectrometry. The constituents forming part of the complex through adsorption onto the different types of particle may then be identified.

As stated above, embodiments of the present invention comprise the use of a mass spectrometric technique to analysis at least one constituent e.g. a constituent which has been separated from a sample deposited on a surface.

The mass spectrometric technique may be any technique which can be used to identify at least one constituent of a sample e.g. a biological sample. The mass spectrometric technique may be an ionisation-based technique e.g. a matrix associated mass spectrometric technique. Samples prepared according to the methods of this invention may be analysed with any mass spectrometer in which the ionisation technique allows selective ionisation of a sample on a specific region of a surface. Suitable ionisation techniques include, without limitation, matrix assisted laser desorption ionisation (MALDI), surface assisted laser desorption ionisation (SALDI), fast atom bombardment (FAB), secondary ion mass spectrometry (SIMS), desorption electrospray ionisation (DESI), desorption sonic spray ionisation (DeSSI), a direct analysis in real-time (DART) ion source, or an atmospheric solids analysis probe (ASAP). Thus, in one embodiment, the mass spectrometric technique is selected from MALDI, SALDI, FAB, SIMS, DESI, DeSSI, DART and ASAP. In one embodiment, the mass spectrometric technique is selected from MALDI and SALDI, e.g. MALDI-TOF-MS and SALDI-TOF-MS.

Typically, in MALDI the sample is co-deposited with a matrix material. The matrix agent e.g a solution comprising 2,5-dihydroxybenzoic acid (DHB) that is capable of absorbing energy from the laser used in the technique. Alternatively, the matrix agent may be selected from e.g. derivatives of benzoic acid, cinnamic acid, and related aromatic compounds, e.g. 2,5-dihydroxybenzoic acid (2,5-DHB or gentisic acid), [alpha]-cyano-4-hydroxy cinnamic acid (CHCA), 3,5-dimethoxy-4-hydroxy cinnamic acid (sinapic acid, sinapinic acid or SPA), nicotinic acid, picolinic acid, trans-3-methoxy-4-hydroxy cinnamic acid (ferulic acid) 2-(4-hydroxyphenylazo)-benzoic acid (HABA), 6-aza-2-thiothymine (ATT), 3-HPA, succinic acid, glycerol, 4-hydroxypicolinic acid, tartaric acid, glycerine, 2,4,6-trihydroxy acetophenone, 3-hydroxypicolinic acid, 3-aminoquinoline, 1,8,9-trihydroxy-anthracene (dithranol), the laser dye coumarin 120, substituted pyrimidines, pyridines, and anilines, e.g. para-nitroaniline.

However, in preferred embodiments the matrix agent is an affinity material as described herein. The photons from laser pulses are absorbed by the matrix molecules, with the energy gained in this process ultimately resulting in desorption and ionisation of the analyte species in the sample, typically generating pseudomolecular ions. MALDI can be used with samples under vacuum ionisation or at atmospheric pressure. SALDI is similar to MALDI, except that rather than using a crystalline matrix, a suspension of a solid in a non-volatile liquid, for example a fine graphite powder in glycerol, is used as the matrix that is mixed with the analyte. Another example of SALDI agents are the silica particles described herein. In one embodiment, the method comprises the use of silica particles as described herein as affinity materials together with a matrix agent such as CHCA.

In one embodiment, the mass spectrometric technique is FAB. Typically, in FAB the material to be analysed is mixed with a non-volatile matrix, generally a liquid with low volatility, such as glycerol, thioglycerol or 3-nitrobenzyl alcohol. Alternatively, the affinity materials described herein may be used as the matrix. The sample is then placed into a vacuum source and bombarded with a high energy beam of atoms generating ions from the sample that can be analysed by the mass spectrometer. The beam of atoms is typically formed from a mono atomic inert gas, such as argon or xenon. SIMS is similar to FAB, but uses a beam of primary ions, such as $Cs^+$, to bombard the sample containing the matrix and analyte, in place of the beam of fast atoms.

Other ionisation techniques commonly used to form ions from a surface for analysis by mass spectrometry utilise atmospheric pressure sources and involve directing various species against the surface to generate ions from the sample. In one embodiment, the mass spectrometric technique is DESI. In DESI an electrospray source is used to create charged droplets that are directed at the solid sample. The charged droplets are able to pick up molecules from the sample through interaction with the surface and then form ions from the sample that can be directed into the analyser of a mass spectrometer.

In one embodiment, the mass spectrometric technique is DeSSI. In DeSSI sonic spray ionisation is used in place of electrospray ionisation to form the ions that are directed at the sample surface. In one embodiment, the mass spectrometric technique is DART. In DART an excited state gas stream is formed from a gas by glow discharge. The excited state gas atoms or molecules, for example of helium or nitrogen, are then directed against the sample surface, where they interact with the sample to desorb and ionise the compounds it contains, with the resulting ions then directed into the analyser of the mass spectrometer. In one embodiment, the mass spectrometric technique is ASAP. In ASAP a jet of heated gas is directed at the sample surface and the desorbed species are ionised by corona discharge.

After the ions have been formed in the ion source, they can be analysed using any suitable mass spectrometric analyser. Suitable mass analysers include those based upon time of flight (TOF), quadrupole (Q), magnetic sector (B) quadrupole or linear ion trap (IT), fourier transform ion cyclotron resonance (FTICR) or obitrap technology, or combination instruments such as triple quadrupole, Q-TOF, IT-orbitrap, IT-FTICR. For example, particularly suitable combinations of ionisation technique and analyser are provided by MALDI-TOF, SALDI-TOF, DART-IT or DESI-IT.

In one embodiment, the mass spectrometric technique may be selected from MALDI-TOF-MS and SALDI-TOF-MS.

Thus, in one embodiment, the surface on which the sample is deposited is a sample support. Typically, a sample support e.g. MALDI-TOF-MS or SALDI-TOF-MS sample support tends to be a plate, for example, a stainless steel plate, which is designed to fit into an MS system. The plate may comprise a well or plurality of wells to which a sample is added. In one embodiment, the method comprises separating the first affinity material/constituent complex to a well which is distinct from the well or other area on the support in which the remaining sample is situated.

In one embodiment, the method comprises the use of at least one particulate affinity material which is also capable of acting as an enhancing agent e.g. a SALDI-assisting agent for mass spectrometric techniques. As a result, the method may be quicker and less expensive as fewer materials are required to analyse the constituents of the sample. Either the first and/or the second particulate affinity material may be suitable as a matrix agent It will be recalled that, in the SALDI-TOF-MS process, the analyte is ionised via determinants on the surface of the particles which donates or receives electrons to or from the target analyte. Thus, in one embodiment, at least one of the particulate affinity materials is used as an agent that, when stimulated by a laser, the components within the particles assist in the ionisation process so that the class of target constituent adsorbed on the particle can be analysed directly on the particle surface. Generally, in SALDI-TOF-MS, the analyte molecules must be in close contact with the surface of the particles.

Prior art methods of analysing the constituents in fingerprints include those disclosed in WO 2007/017701, which is hereby incorporated herein by reference. The MALDI or SALDI-agents described therein are used to analysis those constituents which bind to hydrophobic silica particles. However, other constituents, such as polar amino acids, often do not bind sufficiently to the hydrophobic silica particles to enable analysis to be carried out by mass spectrometry. Thus, in one embodiment, the present invention may be used to analyse amino acid residues and peptides which tend not to bind to hydrophobic silica particles. In one embodiment, these constituents bind to a hydrophilic silica particle as described herein.

Embodiments of the present invention aim to overcome this limitation by providing a method which separates constituents of a biological sample out so that mass spectrometric analysis can be carried on a variety of constituents including those which are not capable of interaction with hydrophobic silica particles as well as those classes of constituents which do bind to hydrophobic particles. Furthermore, in some embodiments, the method does not require separation of the constituent from the affinity material prior to analysis by a mass spectrometric technique, which reduces the number of steps of the method.

In one embodiment, at least the first particulate affinity material includes silica particles which are capable of acting as a matrix agent in a mass spectrometric technique. In one embodiment, the silica particle is hydrophobic and is capable of forming a complex with a constituent of the sample via hydrophobic interaction. Further details of a class of suitable affinity materials are as follows:

In one embodiment, the first affinity material or the second affinity material is a hydrophobic silica particle. Such a particle may be an organically modified silica particle. Details of a suitable process for the manufacture of hydrophobic silica particles can be found for example in PCT/GB2006/050233 (WO 2007/017700) and also WO2007/017701 both herein incorporated by reference in their entirety.

A preparative method of hydrophobic silica particles is described in PCT/GB2006/050233 and which comprises reacting together in a single step a mixture of (1) silane ether monomers, for example, a alkoxysilane and (2) organically substituted silane ether monomers, for example a phenyl modified silicate, with a hydrolysing agent e.g. ammonium hydroxide or another alkali. The silane ether monomers may be tetraalkoxysilanes (abbreviated herein to TAOS). The TAOS's are particularly selected from TEOS (tetraethoxysilane) or TMOS (tetramethoxysilane).

The reaction may be performed at ambient temperature and for a period of 12 to 18 hours in a medium which comprises water miscible solvent, for example ethanol, and water. It is believed that the earlier a reaction is stopped, the smaller the particles which are formed. The silane ether monomer and the organically substituted silane ether monomer may be used in ratios (PTEOS:TAOS) of 1:1 v/v.

The hydrophobic silica particles produced by the above method tend to be predominantly nanoparticles, that is to say, of an average diameter of approximately 40 nm to about 900 nm, typically about 200 nm to about 900 nm, typically about 300 nm to 800 nm and particularly 400 nm to 500 nm. These nanoparticles can be subsequently processed to form microparticles, which can be considered coalesced nanoparticles. The microparticles may be produced using a method which for example comprises the following steps:
i) centrifuging a suspension of particles;
ii) transferring the suspension of hydrophobic silica particles into an aqueous phase;
iii) extracting the suspension from the aqueous phase into an organic phase;
iv) evaporating the organic phase; and
v) crushing and sieving the product obtained in (iv).

Thus, exemplary silica particles are microparticles obtained by reacting monomers as described above and forming a suspension of particles which are centrifuged, extracted into dichloromethane from water, and then dried by evaporation of the organic phase to yield a glass-like sheet of coalesced particles. This is crushed and sieved to obtain particles of the desired size, e.g. of from 1 to 100 µm, more often 10 to 100 µm, for example from 30 µm to 90 µm.

The organic phase preferably comprises an organic solvent which is non-polar or has low polarity. The organic phase may be dichloromethane or another organic solvent for example alkanes, e.g. hexane, toluene, ethyl acetate, chloroform and diethyl ether.

Alternatively, hydrophobic silica microparticles can be obtained from a reaction product containing hydrophobic silica nanoparticles using a method comprising:
(a) centrifuging the reaction product; and
(b) washing the reaction product in a fluid.

The method may comprise repeating steps (a) and (b) a plurality of times. Preferably, the fluid is an aqueous:solvent mixture and is typically a water:organic solvent mixture. Typically, the organic solvent is ethanol. Preferably the initial fluid comprises a mixture of water and organic solvent at a ratio of from about 60 (water):40 (solvent) to about a 40:60 v/v mixture. In other embodiments, the solvent can be, for example, dimethylformamide, n-propanol or iso-propanol.

Typically, the proportion of solvent in the mixture is increased between the initial washing (i.e. suspension) (b) and the final washing (suspension). To obtain microparticles which are coalesced nanoparticles, the final suspension is dried. The microparticles may then be sieved. Once sieved, the microparticles are ready for use.

The microparticles may be considered to be aggregates of smaller silica nanoparticles.

Thus, in one embodiment, the silica microparticles have an average diameter of at least 10 µm, typically at least 20 µm. Typically, the microparticles have an average diameter of from about 30-90 µm. In some embodiments, the microparticles have an average diameter of between about 45-65 µm or from about 65 to 90 µm.

In one embodiment, the particles included in the first and/or second affinity material are nanoparticles (<100 nm in diameter), other sub-micron particles or microparticles. In one embodiment, the particles have an average diameter of ≤100 µm, for example a diameter of ≤1 µm. In one embodiment, the particles have an average diameter from about 10 nm to about 100 µm.

Such hydrophobic silica particles may be stored in a suspension. The fluid may be an ethanolic aqueous suspension. Alternatively, other organic solvents may be used in place of ethanol in the suspension e.g. dimethylformamide, n-propanol or iso-propanol. This suspension can then by applied to the sample and the sample mixed with the particles in the suspension.

Alternatively, the hydrophobic silica particles can be obtained using other methods in the art, (see for example, Tapec et al NanoSci. Nanotech. 2002. Vol. 2. No. 3/4 pp 405-409; E. R. Menzel, S. M Savoy, S. J. Ulvick, K. H. Cheng, R. H. Murdock and M. R. Suddduth, Photoluminescent Semiconductor Nanocrystals for Fingerprint Detection, Journal of Forensic Sciences (1999) 545-551; and E. R. Menzel, M. Takatsu, R. H. Murdock, K. Bouldin and K. H. Cheng, Photoluminescent CdS/Dendrimer Nanocomposites for Fingerprint Detection, Journal of Forensic Sciences (2000) 770-773).

The term "average diameter" can be taken to mean a "mean diameter" of particles typically formed from the methods of the invention. The term "mean" is a statistical term that is essentially the sum of all the diameters measured divided by the number of particles used in such measurements. The diameters of nanoparticles can be estimated from SEM pictures and the scale used in pictures, and for microparticles the diameter can be estimated from a combination of the sieve size, the results from particle size distribution measurements and from SEM pictures. One way a mean diameter can be determined is by using a Malvern Mastersizer (Malvern Instruments Ltd.)

In one embodiment, the affinity material (either the first and/or the second affinity materials) may include silica particles that are modified so as to interact with polar compounds. An example of a suitable class of silica particles is those disclosed in WO 2008/035124. In one class of embodiments, the polar organic moiety is incorporated into the silica particle by using in the synthesis an organically modified silane monomer comprising an organic moiety having the characteristics desired in the end product particles, for example the organic moiety may be a polar organic moiety such as, for example, a heterocycle or a carbocycle substituted by a functional group.

In one embodiment, the heteroatom is introduced into the organic moiety after preparation of the silica particles. For example, functional groups or other heteroatom-containing groups (e.g. heterocycles) may be introduced using conventional functional group chemistry and/or functional group transformations may be performed as known to the skilled chemist. By way of example, aromatic compounds may be substituted using, for example, aromatic substitution reactions familiar to the skilled chemist. For example, aromatic moieties contained in silica particles may be nitrated using a mixture of concentrated nitric and sulphuric acids. If desired, the nitro group may be reduced to an amino group. The amino group may in turn be diazotised and used to prepare azo-bridged derivatives with phenols and related compounds, for example phenol or tyrosine. Aromatic compounds may be halogenated by the action of halogen in the presence of a Lewis acid or, in the case of fluorine, using the techniques commonly known to organofluorine chemists. Aromatic compounds may be converted to phenyls by reaction with sulphuric acid to create the corresponding aromatic sulphuric acid, followed by fusion with alkali (e.g. KOH).

In the other methods, functional groups or other groups capable of participating in a desired non-hydrophobic interaction are added and/or transformed at an intermediate step in the preparation, e.g. after preparation of organically-substituted silicon nanoparticles but prior to their coalescence into microparticles.

After preparation of the derivatised particles, i.e. after addition of the desired functional group, the particles are conveniently separated from the reaction medium, e.g. by centrifugation, and then washed. After washing, the particles may be crowned and crushed, and optionally sieved.

In one embodiment, at least one type of particulate affinity material may include hydrophilic silica particles. In one embodiment, the affinity material includes 3-Aminopropyl-triethoxysilane (APTES) modified silica particles. APTES modified silica particles are made by a similar process to that described above in respect of hydrophobic silica particles. However, during the manufacture process, APTES is incorporated into the monomer mixture in place of PTEOS. The ratio of the monomers may be for example 1:1 v/v of APTES:TEOS (2.5 ml:2.5 ml) similar to the usual (2.5 ml:2.5 ml) PTEOS:TEOS ratio.

At least the first particulate affinity material should be magnetic to enable separation of a constituent from the sample. In one embodiment, the first affinity material includes magnetic particles e.g. magnetic silica particles. The silica particles may comprise magnetic or paramagnetic particles. The magnetic and/or paramagnetic particles may be any magnetic or paramagnetic component, for example, metals, metal nitrides, and metal oxides. Examples of magnetic metals include iron, whilst examples of a metal oxide include magnetite and haematite. The magnetic particles may be incorporated into the silica particles during the manufacture process.

In one embodiment, the method includes locating a magnetic element with respect to the sample. The magnetic element may be a magnetic wand. Examples of magnetic wands are available from Crime Scene Investigation Equipment Ltd., (formerly K9 Scenes of Crime Ltd.) Northampton, UK. In one embodiment, the magnetic element is moved in a direction away from the sample, thus dragging the first affinity material/constituent complex away from the remainder of the sample, thus separating at least one constituent from the sample.

In one embodiment, one or more types of particulate affinity materials may incorporate a dye or coloured particle for visualisation purposes. In one embodiment, each affinity material may include a dye or coloured particle that is different from other types of affinity material. The use of differing visualization means e.g. a dye or coloured particle can be used to distinguish classes of affinity materials which have differing properties. Thus, in an exemplary embodiment, a first type of affinity material e.g. an APTES-modified silica particle may comprise fluorescein, whilst a second type of affinity material e.g. a hydrophobic silica particle, includes, for example, thiazole orange. Coloured particles which may be included in the particulate affinity material include carbon black, titanium dioxide, magnetite, crystal violet, and methylene blue. These coloured particles may be incorporated into the silica particle during its manufacturing process.

In an embodiment, the dye to be incorporated into the particle can be for example a coloured or a fluorescent dye. Examples of dyes included in the scope of the invention are, although not limited to, fluorescein derivatives for example Oregon Green, Tokyo Green, SNAFL, and carboxynaptho-fluorescein, rhodamine (e.g rhodamine B and rhodamine 6G) and analogues thereof, thiazole orange, oxazine perchlorate, methylene blue, basic yellow 40, basic red 28, and crystal violet, and analogs thereof. Without being bound by scientific theory, it is considered that dyes which are positively charged, for example, rhodamine, are better incorporated when PTEOS is used in the method than dyes which comprise anionic or cationic group such as carboxylic groups. Examples of other dyes which could be used in the invention include those which possess a planar aromatic substructure and positively charged functional groups (e.g. ethidium bromide and other DNA intercalating agents). In one embodiment, an APTES modified silica particle does not include a dye.

Preferably the dye is included in the reaction mixture of silane monomers.

Exemplary dyes include fluorescein, oxazine perchlorate, methylene blue, basic yellow 40, thiazole orange and basic red 28 and rhodamine e.g. rhodamine B and rhodamine-6G.

In one embodiment, the particulate affinity material comprises a metal component, a metal oxide, carbon and/or a metal nitride. In one embodiment, the particulate affinity material comprises silica particles which comprise a metal component, a metal oxide, carbon and/or a metal nitride. Alternatively, the particulate affinity material may comprise metal particles in addition to the silica particles. In one embodiment, the particulate affinity material comprises carbon black embedded therein. In some embodiments, this class of particulate affinity material is suitable for use as a matrix agent. In one embodiment, the particulate affinity material comprises silica particles obtained from a method which comprises use of a starting ratio of carbon black: phenyltriethoxysilane of 1:2. In one embodiment, the particulate affinity material may be hydrophobic or hydrophilic.

The method and kit of the present invention may be used to identify constituents of a sample. Exemplary samples include plasma, saliva, urine, and latent fingerprints and earprints and any residue left following contact between a surface and part of a person's skin e.g. a footprint. The sample may be a print, a "lifted" fingerprint, a sample taken from a print and/or which includes materials taken from a latent fingerprint and which includes e.g. constituents of a latent fingerprint.

A "lifted" fingerprint is a fingerprint comprised of material which has been transferred from a fingerprint, e.g. a latent fingerprint which has been deposited on a substrate, to a second surface. In one embodiment, the term "lifted fingerprint" refers to residues of a latent fingerprint which have been transferred from the surface on which the latent fingerprint has been deposited. A lifted fingerprint need not necessarily show the pattern of a fingerprint and may be comprised of the constituents making up the fingerprint.

The present invention may comprise interrogating the affinity material/constituent complex e.g. a first complex by a mass spectrometric technique to determine at least one property of the constituent. In one embodiment, the constituent adheres to the affinity material such that ionisation of the constituents occurs when the complex is interrogated by an ionisation based mass spectrometric technique.

The constituents of the fingerprint which may be detected using the method of the present invention include, for example, (1) endogenous residues e.g. cholesterol, squalene, fatty acids, wax esters, proteins, peptides, amino acids and DNA; (2) contact residues e.g. residues from a narcotic e.g. cocaine and/or residues from ballistics/explosives, and (3) exogenous metabolites e.g. nicotine metabolites and drug metabolites.

In one embodiment, the sample is a latent fingerprint. The constituents detected and/or identified by the present invention include (1) an endogenously produced substance e.g. proteins, lipids, DNA, peptides and/or endogenously derived metabolites which is present as a constituent included in a latent fingerprint; (2) an exogenous compound or metabolite which is present as a constituent included in a fingerprint; and/or (3) a contact residue which is present on or within a fingerprint.

Examples of the types of target constituent to be identified include for example (1) squalene and cholesterol; (2) cocaine and its metabolites and nicotine and its metabolite and (3) ballistic residues from e.g. firearms and/or explosives, residues from handling drugs of abuse (narcotics) e.g. cocaine.

Other examples of endogenous residues which may be identified by the method include for example endogenous substances (e.g. squalene, cholesterol, waxes and esters, steroids e.g. estrogens and testosterone and markers of age, gender, skin colouration, diet, and health) which may be secreted through skin pores and deposited with other chemicals within the fingerprint. Substances derived from an individual's diet may be detected by the method described herein. The method may also be used to detect the metabolites and conjugates of the aforementioned. Examples of endogenous residues may also include exogenous metabolites for example drug and their metabolites including drugs of abuse and their metabolites, prescribed drugs and metabolites and compounds derived from dietary sources or breakdown products of the same. The method could also be applied to the proteomic or genomic analysis of the cells (e.g shed skin cells) or DNA respectively located within the developed print. The method may also be used to detect other contact residues for example, illegal drugs e.g. narcotics, explosive material, for example, material used in bomb making processes, and residue from the use of a fire arm.

The method of the present invention may also be used to analyse a variety of residues which may be found on a fingerprint or earprint. Thus, in an embodiment, the method may be used to develop and analyze latent fingerprints from smokers. It is well established that nicotine is extensively metabolised to cotinine in vivo and there is evidence that both nicotine and cotinine are excreted together in sweat. In one embodiment, the method described herein may be used to detect or determine whether a person has handled or ingested drugs of abuse, for example, cocaine.

In one embodiment, at least one endogenous residue and at least one contact residue are co-deposited within the fingerprint.

One class of methods seeks to determine the presence or absence of a predetermined substance. In this case, the mass spectrum is examined for the presence of one or more peaks associated with this known substance. Another class of methods seeks to identify one or more substances in a print by comparing peaks in the mass spectrum with a database or library of peaks.

EXAMPLES

An example of a method of the invention is described for separation and concentration of a polar compound (the amino acid, alanine) and a hydrophobic compound (squalene) which are found in fingerprints, which serves as an example of a biological sample containing a range of complex constituents.

A mixture of these two compounds (hydrophilic and hydrophobic component) is pre-dispensed as a solution onto a stainless steel target plate designed for use in a MALDI-TOF-MS system, and the solvent allowed to air dry. A suspension of the two types of particles is then applied to the residue of the mixture on the surface of the plate. A magnetic wand can then be used to stir the particles, which reconstitutes the two components into the solvent/buffer used to apply the suspension mixture. Selective adsorption of the two analytes takes place onto one or other of the particle types during this selective extraction/pre-concentration incubation step which takes about 1 minute. The magnetisable component can then be dragged away from the site of the original residue using the magnetic wand and these particles deposited on the plate at a new site on removal of the magnet, leaving the non-magnetisable particles at the original site. The solvent can then be dried and the plate placed into the mass spectrometer and the two sites of separated particles interrogated by SALDI-TOF-MS or MALDI-TOF-MS.

Example 1

Separation and MS of a Mixture of Squalene and Alanine Using Magnetisable Hydrophobic Silica Sub-Micron Particles and CHCA as Matrices A mixture of squalene (dissolved in ethanol) and alanine (dissolved in distilled water) was added as a solution, equivalent to 100 ng each, to the surface of a stainless steel MALDI-TOF-MS plate (Shimadzu) and allowed to evaporate under ambient conditions.

To this residue was added a suspension of magnetisable hydrophobic silica sub-micron particles in ethanol. This was prepared by adding ethanol dropwise until a non-viscous homogeneous suspension of particles was produced on shaking that could be easily dispensed onto samples.

Hydrophobic Particle Production

Details of these particles and how they are made can be found in for example WO 2007/017700 and WO 2007/017701. In brief, ethanol (99.7%) was purchased from Hayman Ltd., UK. Tetraethoxysilane (98%+) was purchased from Aldrich, Dorset, UK. Phenyltriethoxysilane was supplied by Fluorochem, Derbyshire UK.

The basic method for the preparation of blank micro- or nanoparticles involves mixing; 30 ml ethanol, 5 ml deionised $H_2O$, 2.5 ml each of tetraethoxysilane (TEOS) and 2.5 ml phenyltriethoxysilane (PTEOS) in a centrifuge tube. To this mixture add 2 ml ammonium hydroxide solution (20% w/v) and rotate the solution overnight. After this time, centrifuge the suspension (3 minutes at 3,000 rpm).

To obtain microparticles, the suspension was subject to centrifugation and liquid/liquid phase extraction into dichloromethane from water, followed by evaporation of the organic phase to dryness, yielding a glass-like sheet of coalesced particles. This is crushed using a mortar and pestle and the resulting particles sieved through brass test sieves with bronze mesh (Endecot Ltd., London UK) by hand.

The particle size fractions used in this study are 38-45, 45-63 and 63-90 µm. A Malvern Mastersizer (Malvern Instruments Ltd., Malvern, UK) can be used to verify the particle size distributions.

To yield nanoparticles, the suspension is isolated following a series of centrifugation and washing steps using 10:90 v/v ethanol/water and then retained as a suspension in 97:3 v/v water/ethanol. Alternatively, nanoparticles are obtained following two washes with a 50:50 mixture of water:ethanol, followed by a wash using 25:75 mixture of water:

ethanol and a final wash using 0:100 mixture of water:ethanol. The reaction product was then resuspended in as little ethanol as possible to transfer to a drying dish. The suspension was left at room temperature for several days before being kept at a temperature of 37° C. for several days.

For magnetic particles, particulate magnetite is prepared according to published methods and 5 ml of the suspension in water is included in the precursor solution.

After around 1 to 2 minutes, the magnetic silica particles were applied to the sample as a suspension (1-2 µl) using a micropipette. After about 30 seconds, a commercial magnetic wand was used to move the particles over the surface in a stirring motion for about 2 minutes. The wand was then slowly dragged to one side and the magnet retracted to deposit the particles on the surface adjacent to the original site but removed from it. The separated solutions were then allowed to evaporate under ambient conditions.

The MALDI plate included a well which contained components believed to have been moved as a result of adsorption onto the hydrophobic silica particles and was therefore labelled as the hydrophobic well. The MALDI plate included a well at the original site of sample deposition was considered to contain hydrophilic components and was therefore labelled as the hydrophilic well. A solution of the sinapinic acid derivative, α-cyano-4-hydroxycinnamic acid (CHCA) in acetonitrile/0.1% trifluoroacetic acid was added to the original site of application of the mixture and the solvent allowed to evaporate under ambient conditions. The plate was then interrogated using a Shimadzu Axima TOF-MS system in positive mode at the location on the surface where the particles were located and at the location of the original mixture. Details of MALDI-TOF-MS interrogation using the silica particles can be found in for example WO 2007/017701 in the name of University of Sunderland.

Figure 6:
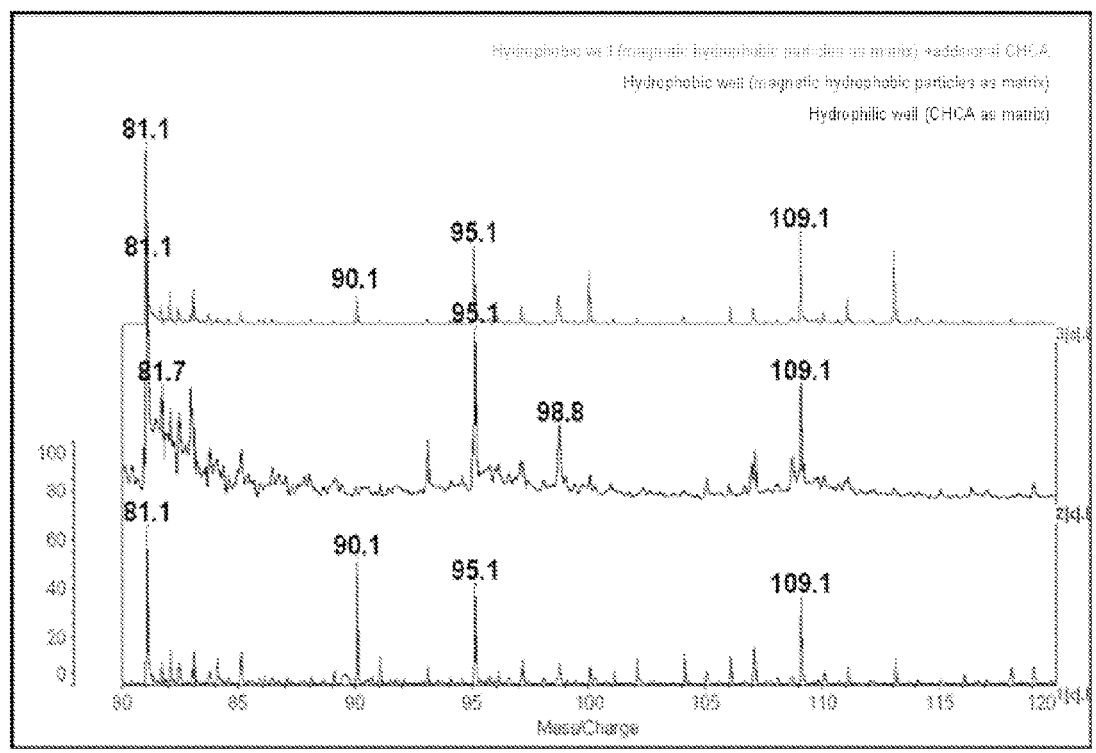
FIG. 6: MALDI-TOF-MS data at the low mass range specifically for alanine peak at 90.1 mu. The upper spectrum represents a hydrophobic well using magnetic hydrophobic silica particles as a matrix together with additional α-cyano-4-hydroxycinnamic acid (CHCA). The middle spectrum represents a hydrophobic well using magnetic hydrophobic silica particles as a matrix. The lower spectrum represents a hydrophilic well using CHCA as a matrix agent.
Figure 7:
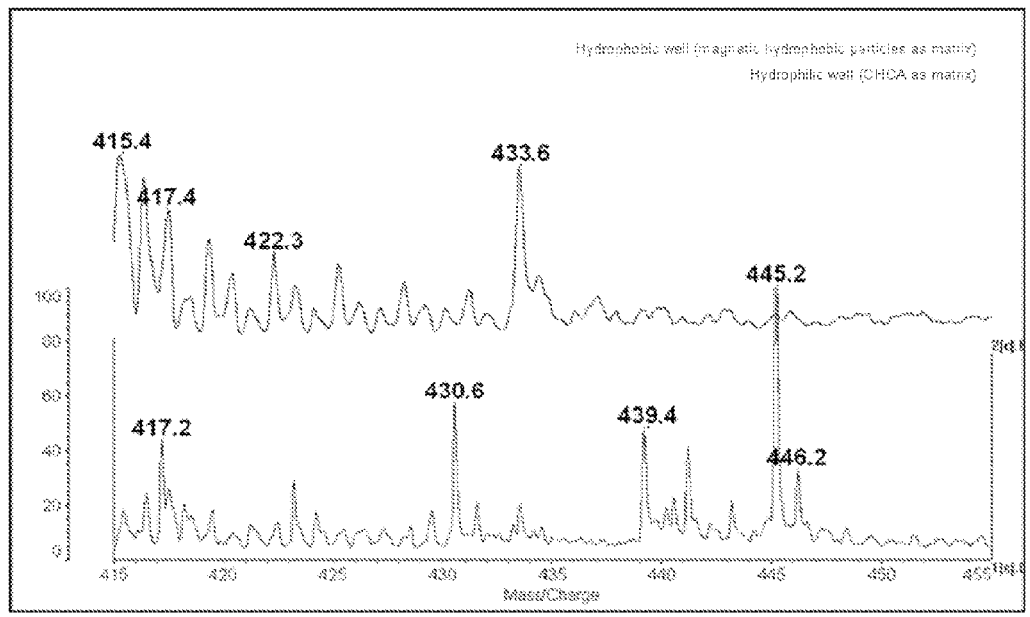
FIG. 7: MALDI-TOF-MS data shown at the higher mass range specifically for sodium adduct-squalene peak at 433.6 mu. The upper spectrum represents a hydrophobic well using magnetic particles as a matrix. The lower spectrum represents a hydrophilic well using CHCA as a matrix.

The resulting combined MS spectra are shown in FIGS. 6 and 7. With reference to FIG. 6, alanine was observed in the hydrophilic well at 90.1 mass units (mu) whilst alanine was not observed in the hydrophobic well. After which, CHCA was added into the hydrophobic well, alanine was then detected in the MS of the hydrophobic well. However intensity of alanine in the hydrophobic well was lowered in comparison to the hydrophilic well. This showed that significant separation of the hydrophilic component, alanine had occurred though incomplete as alanine was still present in a reduced amount in the hydrophobic well.

With reference to FIG. 7, only the peak due to the sodium adduct of squalene was observed in the hydrophobic well, at 433.6 mu. Squalene was not observed in the hydrophilic well. The results show selective and efficient adsorption of squalene onto the magnetisable hydrophobic particles and of the ability of the hydrophobic silica particles to induce ionisation of the adsorbed squalene on laser irradiation. The zwiterionic and highly polar alanine does not bind to these magnetisable hydrophobic particles and remained mostly at the original site, whereas the squalene adsorbed onto the magnetisable particles is removed from this site as the particles are dragged to the new site on the surface.

Example 2

Separation and MS of a Mixture of Squalene and Alanine Using Magnetisable Hydrophobic Silica Sub-Micron Particles and Non-Magnetic Hydrophilic 3-Aminopropyl Triethoxysilane (APTES) Modified Silica Sub-Micron Particles as Matrices The process is similar to Example 1 except APTES-modified silica sub-micron particles were used in place of CHCA as a matrix for interrogation of the hydrophilic well.

35 ml ethanol, 5 ml of de-ionised water, 4 ml TEOS, 3 ml ammonium hydroxide, 3 ml of carbon black suspension in water (15% w/v) were added to a plastic tube. The tube plus screw cap were rotated for 4 hours at ambient temperature when 0.4 ml of APTES was added. The sealed tube was then again inverted for a further 12 hours. The resulting black suspension was isolated and washed as described above for the corresponding hydrophobic carbon black particles. The final step following the last washing in ethanol was to leave the damp material in an oven at 40° C. to dry for at least 4 hours. The resulting particles were about 40-50 nm in diameter.

A mixture of squalene (dissolved in ethanol) and alanine (dissolved in distilled water) was added as a solution, equivalent to 100 ng each, to the surface of a stainless steel MALDI-TOF-MS plate (Shimadzu) and allowed to evaporate under ambient conditions.

To this residue was added a suspension (2-3 µl) consisting of a 1:1 mixture (w/w) of magnetisable hydrophobic silica sub-micron particles and of the APTES-modified silica sub-micron particles in ethanol, formulated as described above. A commercial magnetic wand was used to move the particles over the surface for about 2 minutes. The wand was then slowly dragged to one side and the magnet retracted to deposit the magnetisable hydrophobic particles on the surface adjacent to the original site but removed from it, leaving the hydrophilic particles at the original site. The solutions were then allowed to evaporate under ambient conditions.

The well which contained the magnetisable silica particles was believed to also contain the separated hydrophobic components adsorbed onto the particle surface and is thus labelled as the hydrophobic well while the non-magnetisable hydrophilic particles believed to contain the separated hydrophilic components remain at the well located at original site of sample application which is therefore labelled as the hydrophilic well.

The plate was then interrogated using a Shimadzu Axima TOF-MS system in positive mode at the locations on the surface where the two sets of particles were located. Details of SALDI/MALDI-TOF-MS can be found in for example WO 2007/017701 in the name of University of Sunderland.

Figure 8:
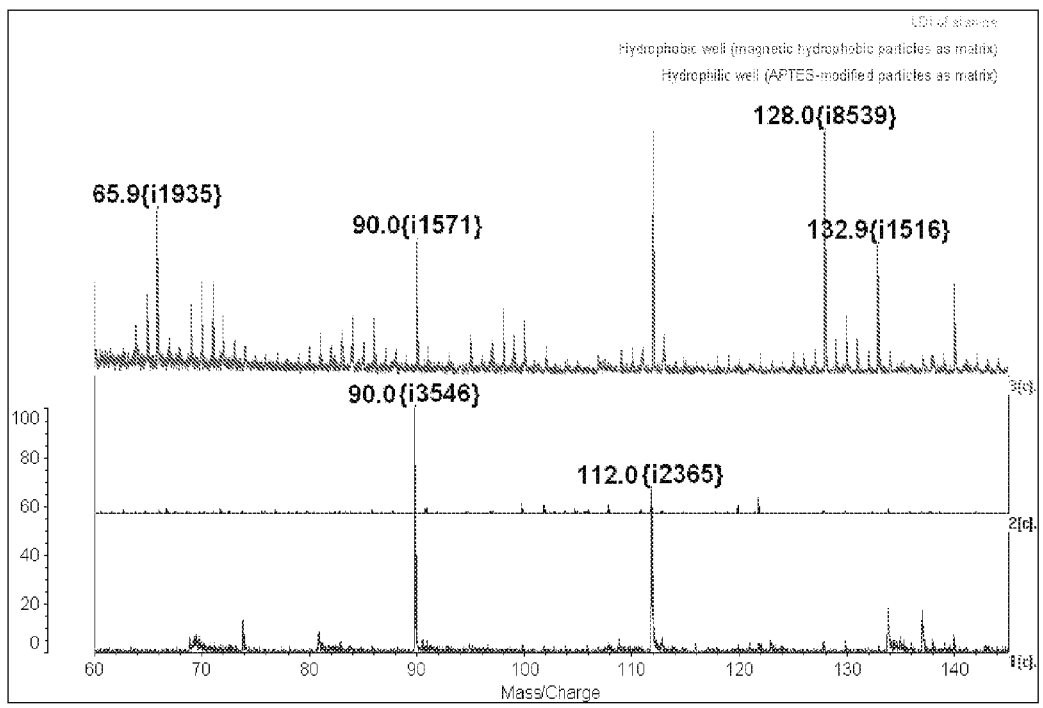
FIG. 8: MALDI-TOF-MS data shown at the low mass range specifically for alanine peak at 90.0 mu. The upper spectrum represents a hydrophobic well using magnetic particles as a matrix. The lower spectrum represents a hydrophilic well using APTES modified silica particles as a matrix.
Figure 9:
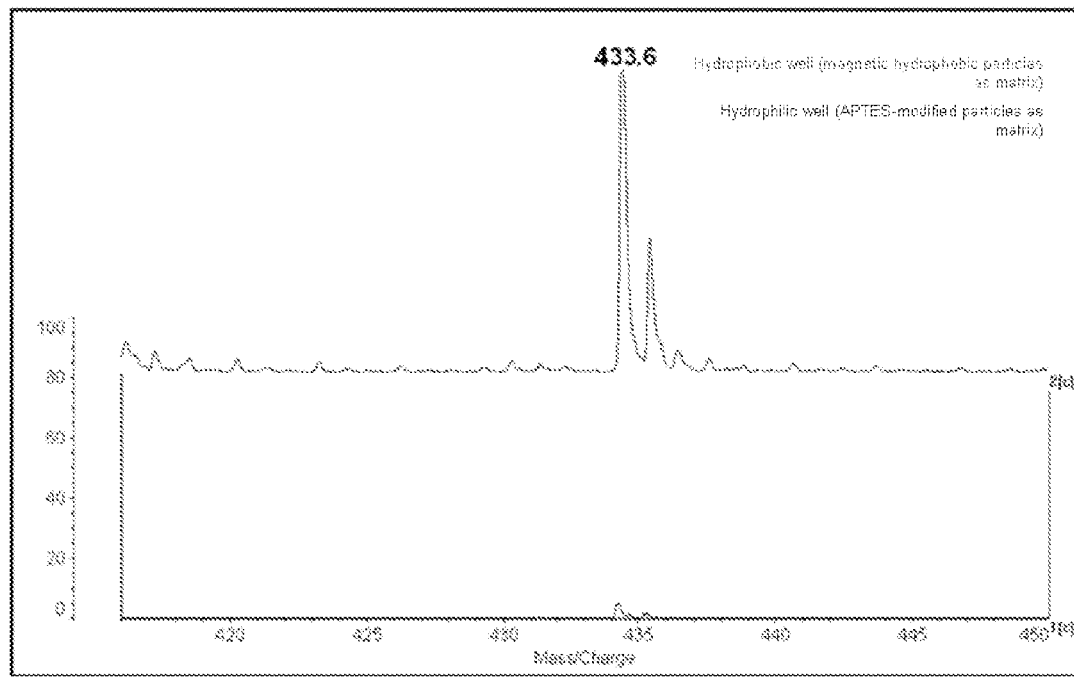
FIG. 9: MALDI-TOF-MS data shown at the higher mass range specifically for sodium adduct-squalene peak at 433.6 mu. The upper spectrum represents a hydrophobic well using magnetic particles as a matrix. The lower spectrum represents a hydrophilic well using APTES-modified silica particles as a matrix.

The resulting combined MS spectra are shown in FIGS. 8 and 9. In FIG. 8, alanine was observed in the hydrophilic well at 90.0 mass units (mu) whilst no alanine peaks were detected in the hydrophobic well. With reference to FIG. 9, only the peak due to the sodium adduct of squalene was observed in the hydrophobic well, at 433.6 mu. Squalene was not observed in the hydrophilic well. The results show selective adsorption of squalene onto the magnetisable hydrophobic particles. In addition, the highly polar alanine is able to interact with the non-magnetic APTES-modified silica particles. In turn, both types of modified silica particles are able to assist the ionization process; APTES-modified silica particles for alanine, and PTEOS-modified silica for squalene in analysis, via SALDI-TOF-MS. APTES-modified silica particles added as a matrix gives an improved intensity signal compared to laser desorption ionisation (LDI) of alanine without added matrix.

Example 3

Separation of Squalene and Alanine in a Latent Fingerprint

A donor rubbed her fingers across the forehead without prior washing of hands and applied her print onto a stainless steel MALDI plate by pressing rubbed finger on the plate. A 400 μl suspension of magnetisable hydrophobic silica submicron particles in ethanol was pipetted onto the print. The suspension covering the print area was stirred using a commercially available magnetic wand by rotating the magnetic wand above the magnetic suspension from above for 30 seconds. After which, using the magnetic wand, the hydrophobic magnetic particles were slowly pulled to one side of the print. CHCA was added to the wells on the other side of the print. Both solvents were allowed to dry and the surface areas interrogated using a Shimadzu Axima TOF-MS system in positive mode.

Figure 10:
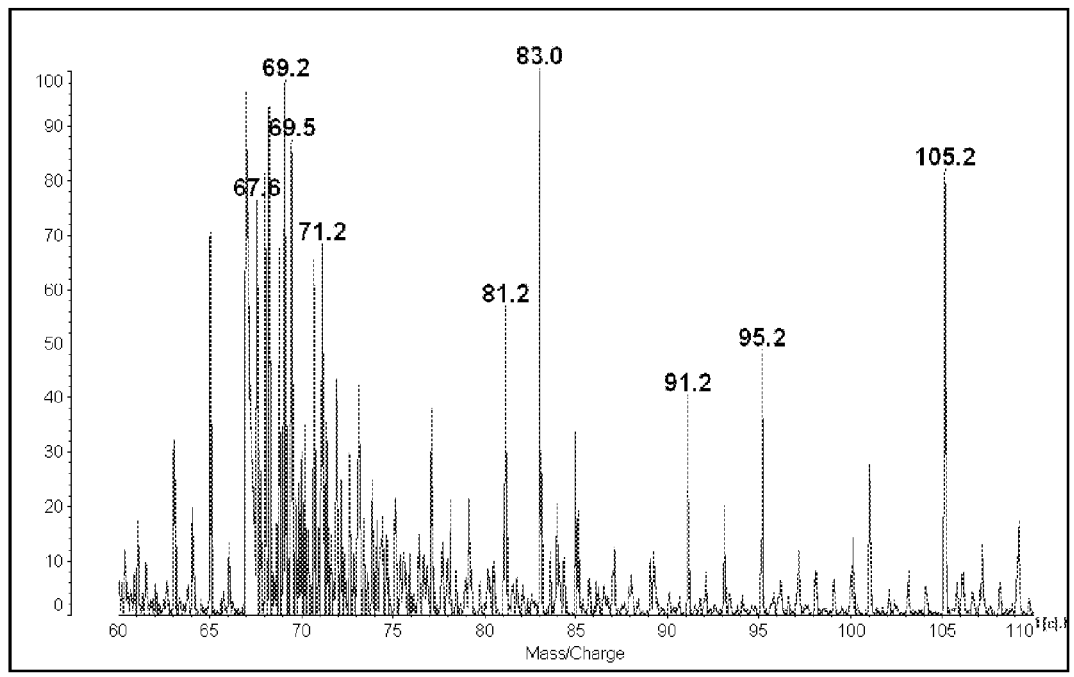
FIG. 10: MALDI-TOF-MS data from a hydrophobic well, using magnetic hydrophobic particles as a matrix, at the low mass range.
Figure 11:
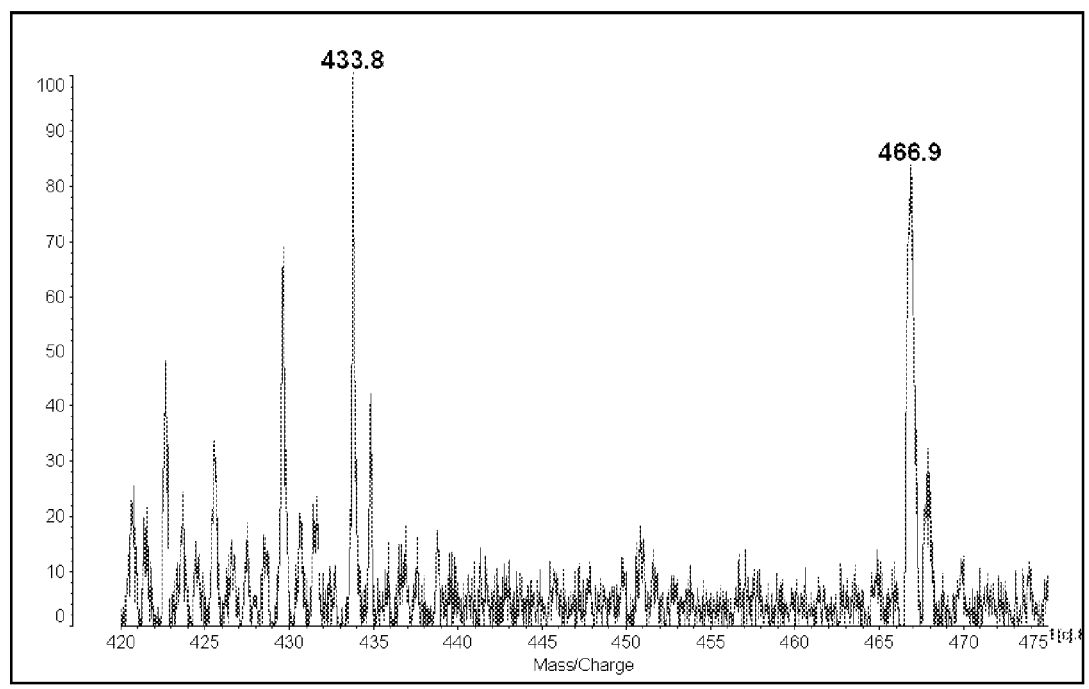
FIG. 11: MALDI-TOF-MS data from a hydrophobic well, using magnetic hydrophobic particles as a matrix, at the higher mass range specifically for sodium adduct-squalene peak at 433.8 mu.

The mass spectra for the area associated with the magnetisable particles are shown in FIGS. 10 (low mass range) and 11 (higher mass range). Squalene was observed at 433.8 mu but alanine peaks were absent on the hydrophobic magnetic particles.

Figure 12:
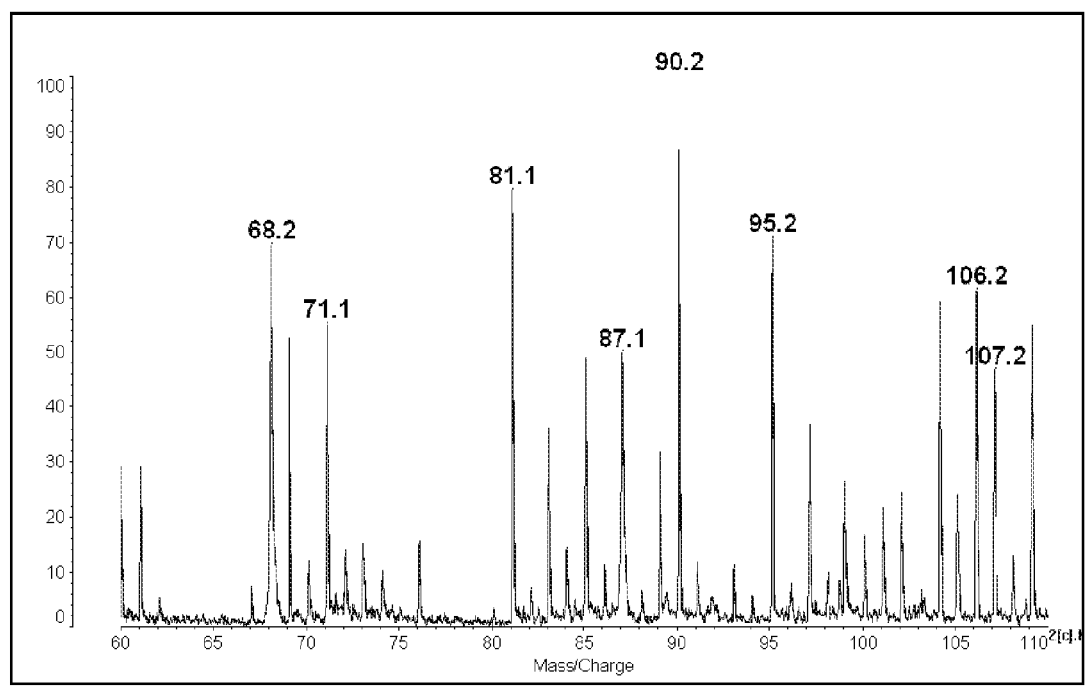
FIG. 12: MALDI-TOF-MS data from a hydrophilic well, using CHCA as a matrix, at the low mass range specifically for alanine peak at 90.2 mu.
Figure 13:
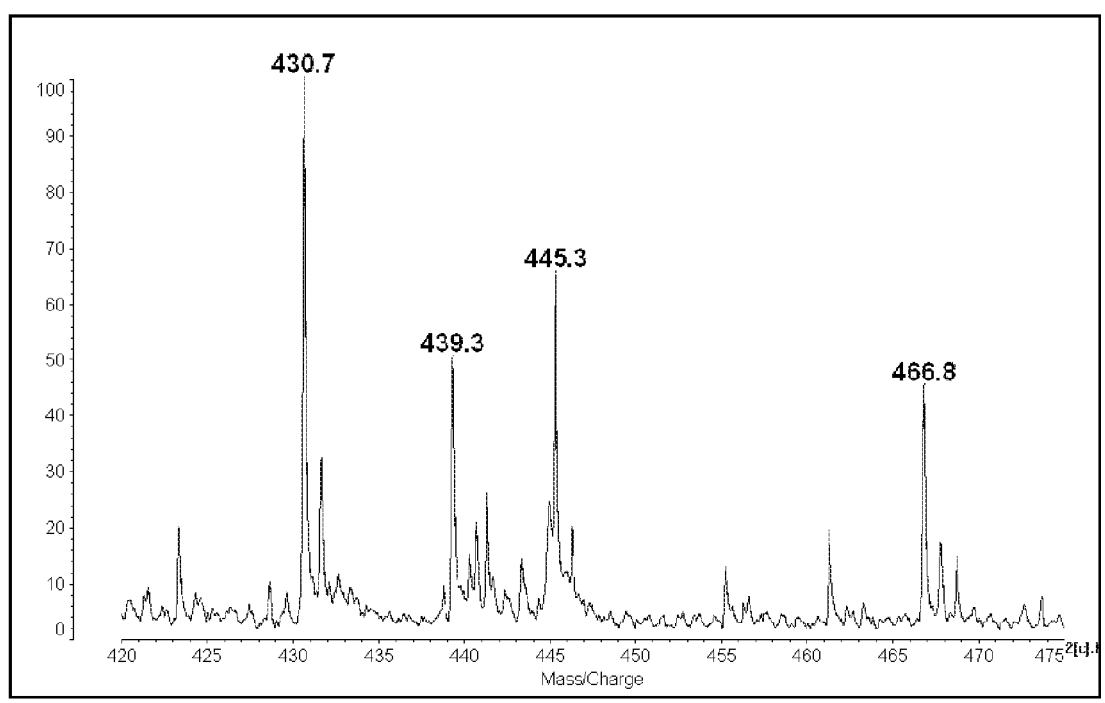
FIG. 13: MALDI-TOF-MS data from a hydrophilic well, using CHCA as a matrix, at the higher mass range

The mass spectra for the area associated with the site of the original print (in the presence of CHCA) are shown in FIG. 12 (low mass range) and FIG. 13 (higher mass range). Alanine was observed at 90.2 mu but squalene peaks were absent.

The results demonstrate that selective adsorption of squalene in a fingerprint occurs onto hydrophobic particles while polar alanine in the print does not adsorb onto these hydrophobic particles. Again the components adsorbed onto magnetisable particles can be separated on the surface using a magnet.

The invention claimed is:

1. A method of preparing and analyzing a complex liquid sample comprising a hydrophilic target constituent and a hydrophobic target constituent, comprising:
    mixing the sample with hydrophilic and hydrophobic silica particles on a plate suitable for MALDI/SALDI analysis to form a first complex between the hydrophilic target constituent and the hydrophilic silica particles and a second complex between the hydrophobic target constituent and the hydrophobic silica particles, wherein either the hydrophilic or the hydrophobic silica particles are functionalized to include a magnetic component;
    separating the first complex from the second complex by selectively positioning at least one magnet with respect to at least one of the first and the second complex and removing one complex from another directly on the plate using the at least one magnet; and
    carrying out a MALDI/SALDI analysis on the separated first complexes, without further addition of a citrate or a MALDI/SALDI matrix,
    wherein the sample is not washed or rinsed after the separation and before carrying out the MALDI/SALDI analysis.

2. The method of claim 1, wherein the hydrophobic silica particles are formed from silane ether monomers and organically modified silane ether monomers in the presence of a hydrolysing agent.

3. The method of claim 1, wherein the hydrophilic silica particles are formed from 3-aminopropyltriethoxysilane (APTES) monomers.

4. The method of claim 1, wherein the hydrophilic silica particles and hydrophobic silica particles are mixed together in a suspension and applied to the sample, wherein the suspension is an ethanolic suspension.

5. The method of claim 1, wherein the hydrophobic silica particles are embedded with carbon black.

6. The method of claim 1, wherein the hydrophilic silica particles are embedded with carbon black.

7. The method of claim 1, wherein the MALDI/SALDI analysis is selected from MALDI-TOF-MS and SALDI-TOF-MS.

8. The method of claim 1, wherein the hydrophilic or the hydrophobic target constituent is selected from the group consisting of a protein, DNA, RNA, a peptide, an amino acid, and an organic compound.

9. The method of claim 1, wherein the sample comprises a fingerprint, a footprint, an earprint, or any residue left on a surface following contact between the surface and a part of a person's skin.

* * * * *